United States Patent [19]
Wilk et al.

[11] Patent Number: 5,071,746
[45] Date of Patent: Dec. 10, 1991

[54] TEST CARRIER FOR ANALYSIS OF A SAMPLE LIQUID, METHOD OF USING A TEST CARRIER AND PROCESS FOR MAKING A TEST CARRIER LAYER

[75] Inventors: Hans-Erich Wilk, Lorsch; Karin Münter, Mannheim; Rolf Lerch, Ilvesheim, all of Fed. Rep. of Germany

[73] Assignee: Boehringer Mannheim GmbH, Mannheim, Fed. Rep. of Germany

[21] Appl. No.: 337,351

[22] Filed: Apr. 13, 1989

[30] Foreign Application Priority Data

Apr. 28, 1988 [DE] Fed. Rep. of Germany ....... 3814370

[51] Int. Cl.⁵ ............................................. G01N 33/535
[52] U.S. Cl. ...................................... 435/7.94; 422/58; 422/61; 422/68.1; 436/524; 436/531; 436/535; 436/536
[58] Field of Search .............................. 422/55, 56, 57; 436/514, 524, 531, 535, 536; 435/7.94

[56] References Cited

U.S. PATENT DOCUMENTS 4,740,468  4/1988  Weng et al. .................... 436/514
4,839,297  6/1989  Freitag et al. .................. 422/55
4,891,313  1/1990  Berger et al. ................... 436/7

Primary Examiner—Christine Nucker
Assistant Examiner—Jeffrey Stucker
Attorney, Agent, or Firm—Felfe & Lynch

[57] ABSTRACT

The present invention provides a test carrier for the analytical determination of a component of a sample liquid with the help of immunological reagents having a conjugate layer (2, 12), which contains a soluble conjugate of a first immunological binding partner with a labelling, a porous fixing layer (3, 13), which contains a second binding partner in carrier-fixed form binding specifically with the first binding partner, and an optical detection layer (8, 18), wherein the fixing layer (3, 13) is constructed in such a manner that the suction speed with which the liquid is transported in it is so high that the time needed for the spreading out of the liquid in the fixing layer is considerably shorter than the incubation time which is needed for the completion of the specific binding reaction between the first binding partner and the second binding partner and the optical detection layer (8, 18) is so fixed on the test carrier (1, 11) that, in a first position, it is not in contact with the fixing layer (3, 13) making possible a liquid exchange but can be brought into a second position in which a liquid exchange between the fixing layer (3, 13) and the optical detection layer (8, 18) can take place.

The present invention also provides a process for the immunological analytical determination of a component of a sample liquid, as well as a process for the production of a fixing layer for a test carrier.

17 Claims, 1 Drawing Sheet

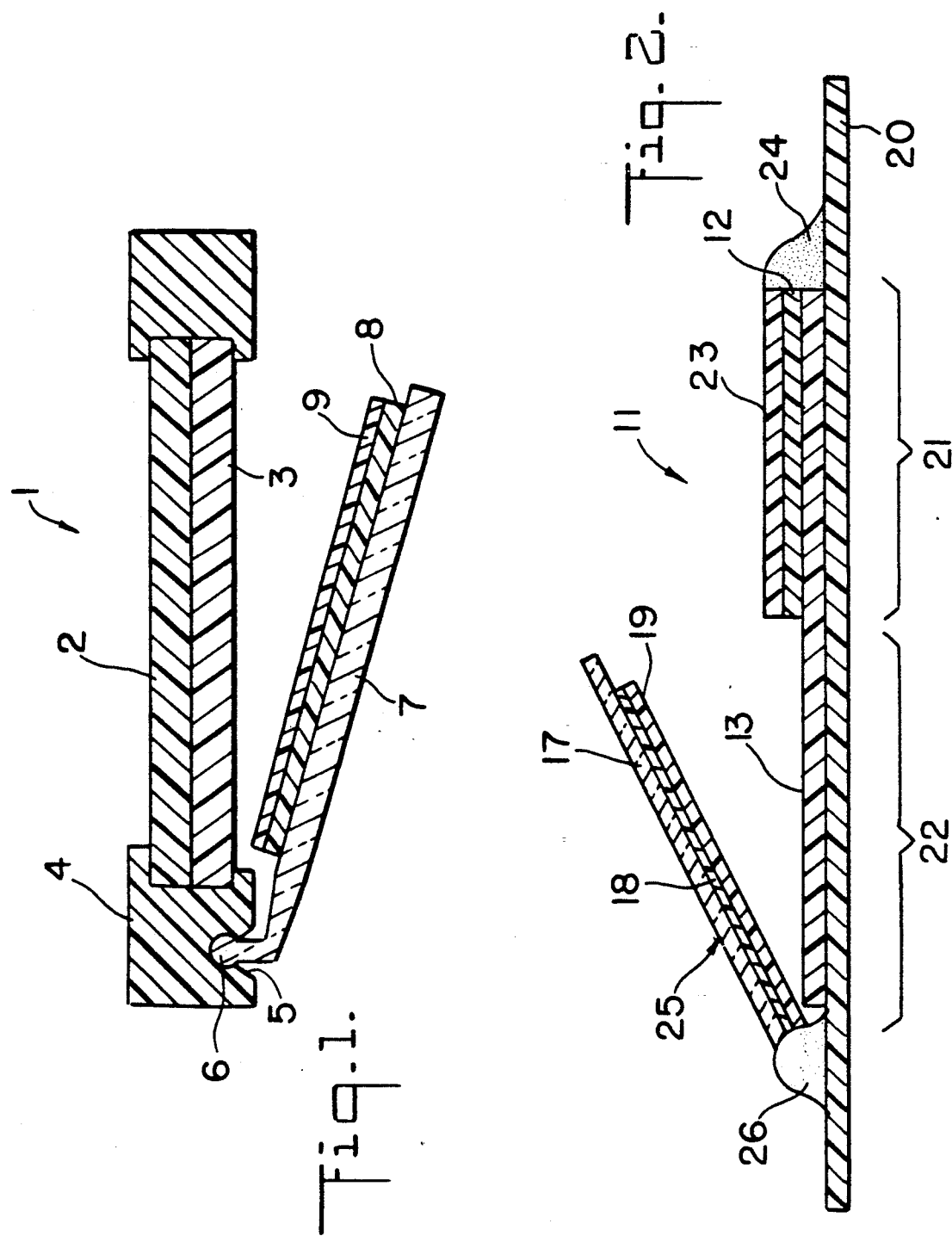

TEST CARRIER FOR ANALYSIS OF A SAMPLE LIQUID, METHOD OF USING A TEST CARRIER AND PROCESS FOR MAKING A TEST CARRIER LAYER

The present invention is concerned with a test carrier for the analytical determination of a component of a sample liquid with the help of immunological reagents having a conjugate layer, which contains a soluble conjugate of a first immunological binding partner and a label, a porous fixing layer which contains a second binding partner in carrier-fixed form and specifically bindable with the first binding partner and an optical detection layer.

Furthermore, the present invention is concerned with a process for the immunological analytical determination of a component of a sample liquid with the help of a test carrier in which a conjugate of a first immunological binding partner and a label, which is contained in a conjugate layer of the test carrier, is dissolved in the sample liquid, the sample liquid with the conjugate of the first immunological binding partner passes into a porous fixing layer which contains a second binding partner in carrier-fixed form is specifically bindable with the first binding partner, a specific binding reaction thereby taking place between the first binding partner and the second binding partner and a part of the conjugate is fixed and the sample liquid with non-fixed conjugate passes into an optical detection layer in which detectable change characteristic for the amount of the non-fixed conjugate which has passed into the optical detection layer.

Furthermore, the present invention is concerned with a process for the production of a fixing layer takes place for test carriers containing a carrier-fixed immunological binding partner.

Immunological processes are playing an increasing role in analysis, especially in the analysis of body fluids, such as blood or urine. They are characterized in that they are highly specific and extremely sensitive. The detection processes are based on the immunological interaction between binding partners specifically bindable with one another, especially antigens (or haptens) and the corresponding antibodies. The component to be determined is frequently itself one of the binding partners. However, there are a plurality of different ways of carrying out the processes in which, in some cases, several immunological binding reactions also take place between different binding partner pairs.

By means of the labelling of one of the binding partners, a measurable signal can be produced which is then used for the desired evaluation. A number of different labels are used in immunological methods. The present invention is directed, in particular, to so-called enzyme immunoassays in which an enzyme is used as label. The enzyme is detected by the same methods as in enzyme diagnosis by allowing the enzyme to act upon a substrate which undergoes an optically detectable change, the optically detectable change usually being a color change. Alternatively, for example, a label with a fluorescent material can be used.

Most immunological detection processes require a plurality of complicated process steps taking place successively and long incubation times. For this reason, for a long time they were carried out exclusively by wet chemical processes either manually or with the help of complicated analysis apparatus.

Recently, so-called "carrier-bound tests" have gained increased importance in the analysis of body fluids. In these tests, reagents are embedded in one or more test layers of a solid test carrier which is brought into contact with the sample. The reaction of sample and reagents usually results in a color change which is evaluated by reflection photometry. The test carrier and the corresponding evaluation devices are, in all, referred to as test carrier analysis systems.

Test carrier analysis systems are characterized, in particular, by simple handling. Furthermore, the devices are comparatively inexpensive so that they can also be used in the laboratory of a general practitioner or in a hospital ward.

Having regard to these advantages, test carriers have already been suggested for immunological determinations. However, considerable difficulties are involved therewith because the reactions taking place on the test carriers do not permit the numerous manipulation procedures which are usually necessary for immunological determinations.

U.S. Pat. No. 4,446,232 describes a simple construction of such a test carrier in which two or three test layers are arranged over one another in such a way that they continuously are in contact with one another, thus making liquid exchange possible. In the case of the three layered embodiment, in the first layer an enzyme conjugate of a first immunological binding partner is present for example an antibody, in the middle layer a second binding partner specifically bindable with the first binding partner, for example an antigen to the antibody, in carrier-fixed form and in the lowermost layer a color-forming substrate for the enzyme.

The course of the test described in this Patent resembles the IEMA test, which is known from wet chemical immunological determinations; an antigen contained in the sample is to complex in the uppermost layer with an antibody-enzyme conjugate. The complexes, as well as non-complexed excess enzyme conjugate, pass into the middle layer where a binding reaction takes place between the excess enzyme conjugate and the carrier-fixed antigen so that the excess enzyme conjugate is fixed (such a layer is referred to as a "fixing layer"). The complexes can migrate through the middle layer and pass into the substrate layer where a color reaction takes place.

This simple transfer of a wet chemical test to a test carrier has not proved to be useful in practice. The liquid flows through the test carrier uncontrollably, whereas in the case of the wet chemical test an exact course of reaction with clearly separated reaction steps is necessary.

Another multilayer construction with securely fixed layers is described in U.S. Pat. No. 4,613,567. This Patent also deals in detail with possible test layer structures.

Federal Republic of Germany Patent Specification No. 34 45 816 describes an immunological test carrier in which several test layers are arranged next to one another on a base layer, the test layers standing in continuous liquid contact with one another via their edges.

It is an object of the present invention to provide a test carrier for immune tests which is simple to use and permits high accuracy in testing. Nevertheless, it to be constructed as simply as possible and to be produced economically.

Thus, according to the present invention, there is provided a test carrier for the analytical determination of a component of a sample liquid with the help of immunological reagents comprising a conjugate layer, which contains a soluble conjugate of a first immunological binding partner and a label, a porous fixing layer, which contains a second binding partner in carrier-fixed form which specifically binds with the first binding partner, and an optical detection layer, wherein the fixing layer is constructed in such a manner that the suction speed with which the liquid is transported into it is so high that the time needed for uniform dispersion of the liquid in the fixing layer is considerably shorter than the incubation time which is needed for the completion of the specific binding reaction between the first binding partner and the second binding partner and the optical detection layer is fixed on the test carrier that, in a first position, it is not in contact with the fixing layer and a liquid exchange therebetween is not possible but the optical detection layer can be brought into second position in which a liquid exchange between the fixing layer and the optical detection layer can take place.

The present invention also provides a process for the immunological analytical determination of a component of a sample liquid with the help of a test carrier in which a conjugate of a first immunological binding partner and a label, which is contained in a conjugate layer of the test carrier, is dissolved in the sample liquid, the sample liquid with the conjugate of the first immunological binding partner passes into a porous fixing layer, which contains in carrier-fixed form a second binding partner specifically bindable with the first binding partner, a specific binding reaction thereby taking place between the first binding partner and the second binding partner and a part of the conjugate is fixed and the sample liquid with non-fixed conjugate passes over into an optical detection layer in which an optically detectable change takes place characteristic for the amount of non-fixed conjugate passing into the optical detection layer. In this process the spreading out of the sample liquid in the fixing layer takes place in a considerably shorter time than the incubation time of the specific binding reaction and the optical detection layer is not in liquid contact with the fixing layer during the incubation time but, after completion of the incubation time, is brought into liquid contact with the fixing layer. The liquid then passes from the fixing layer into the optical detection layer.

The preferred course of the test in the test carrier according to the present invention has a certain similarity to that described in U.S. Pat. No. 4,446,232. If, for example, an antigen contained in a sample liquid is to be determined, then an enzyme conjugate of a corresponding antibody is present in the conjugate layer. The fixing layer contains the sample antigen or an analogue thereto (which binds with the same antibody) in carrier-fixed form. Due to the binding reaction taking place in the fixing layer, conjugate which does not bind with the free antigen from the sample is bound to the carrier-fixed antigen of the fixing layer.

In contradistinction to the previously known test carrier, in this invention, it is not the object that, in the conjugate layer, the binding reaction between the conjugate and the analyte takes place as completely as possible and the fixing of the excess conjugate in the fixing layer takes place as quickly and completely as possible. This would be promoted by a slow absorption in the fixing layer.

On the contrary, in the present invention, it has been ascertained that a high rate of absorption in the fixing layer is to be aimed for so that the liquid spreads out in this layer comparatively quickly. The time needed for the complete spreading out of the liquid is to be short in comparison with the incubation time necessary for completion of the immunological binding reaction taking place in a fixing layer. "Complete reaction" is understood here in the general meaning in chemistry, i.e. that the reaction is complete for practical matters (at least to 95%). This time in each test depends upon the properties of the first and second binding partner. For a particular test carrier, the necessary incubation time of the binding reaction is, consequently, a quantity known to the expert.

With the antigen-antibody pairs today available, incubation times of 1 to 3 minutes are typically sufficient. In this case, the spreading out time of the liquid in the fixing layer is less than 30 seconds and preferably less than 20 seconds, typical values being about 10 seconds. The spreading out time should be at most one third of the incubation time.

The speed of spreading out in the fixing layer is substantially influenced by its suction force and the flow resistance prevailing in the layer. The suction force depends on the properties of the material surface and upon the capillary size. The surface tension of the material surface should be such that the material is wetted by the liquid, i.e. is hydrophilic. In the case of a given surface tension, the suction force is the greater, the smaller are the capillary gaps. On the other hand, however, the flow resistance increases when the capillary gaps in the fixing layer become narrower. On the basis of these general indications, from the plurality of known porous layer materials, the expert can select an appropriate material with a sufficiently high suction force, wherein the liquid spreads out fast enough.

As mentioned hereinbefore, the speed of spreading out in the fixing layer is not dependent only on its suction force. Preferably, however, the suction force should itself be comparatively great and, in particular, should be higher than the suction force of the conjugate layer. Liquid which is supplied to the conjugate layer is thereby absorbed almost completely and comparatively quickly in the fixing layer with which the conjugate layer is preferably in continuous contact, thereby allowing liquid exchange therebetween.

The optical detection layer can be moved manually or with the help of an evaluation device between the first and the second position. Preferably, it is in the second position located above or below the fixing layer in such a manner that the liquid exchange takes place through the adjacent surfaces of the layer vertically to these. The fixing layer can be directly in surface contact to the optical detection layer or there can be one or more porous layers therebetween through which the liquid exchange takes place.

The said requirements for the fixing layer can be fulfilled by means of a plurality of different layer structures. Porous synthetic resin materials with sufficiently larger average pore diameter or papers as basis material for the fixing layer for example, can be used. The fixing layer is preferably based on a fiber composite structure in which the fibers or filaments are so bound that they can be used as starting materials for a test carrier layer. Important examples include the known textile composite structures, such as fabrics and knitted materials.

Especially preferred are layer structures based on a fiber fleece. In such fleece the fibres normally have a fiber preferred direction of orientation. Comparatively rapid spreading out takes place in this direction although the overall material density is comparatively great. Such fleece are preferably produced by a wet process in a hydrodynamic way, i.e. the fleece is consolidated from an aqueous suspension of the corresponding fiber.

The binding partners fixed in the fixing layer can be bound directly to the structure-forming components of the layer. For example, synthetic resin materials from which are produced a porous synthetic resin layer, a synthetic resin fabric or a synthetic resin fibre can be provided by etching with reactive organic groups to which are covalently bound, for example, antigens or antibodies. Such binding processes are well known, reference being made, for example, to Federal Republic of Germany Patent Application 34 45 816 and U.S. Pat. No. 4,613,567.

According to a further embodiment of the present invention, an especially high loading density of the carrier-fixed immunological binding partner can be achieved in which the binding partner is fixed to particles which are embedded in the layer structure of the fixing layer. There can be used not only synthetic resin particles (latex particles) but also particles of inorganic material. In the last-mentioned case, the immunological binding partner is bound via reactive organic groups which have been previously coupled on the inorganic particle structure. The reactive organic groups can, in particular, be amino groups or carboxyl groups to which the immunological binding partner is coupled with the help of an amide binding. Such a coupling for antibodies is described in connection with the production of chromatography columns in several variants in U.S. Pat. No. 4,560,504. Further details for the binding of immune reagents to carrier particles are also known from German Patent Application No. 37 40 471 and corresponding U.S. patent application Ser. No. 07/275,409 to which reference is here expressly made.

The particles can be part of a three-dimensional particle composite structure, such as is described, for example, in U.S. Pat. No. 4,258,001. Further examples are mentioned in U.S. Pat. No. 4,258,001.

However, it is especially preferred that the particles be embedded in a fiber composite structure, especially in a fiber fleece. Such a fixing layer is preferably produced in such a way that, in a first process step, the immunological binding partner is fixed to carrier particles, in a second process step, the particles are separated from the substances needed for fixing the binding partner (by filtration, sedimentation or centrifuging), in a third process step, a material strip consisting of a fiber composite structure is impregnated with a suspension of the carrier particles and, in a fourth process step, the material strip is dried.

In the scope of the present invention, it has been ascertained that the particles in a fixing layer produced according to this process adhere sufficiently so that they, and with them the binding partners bound to their surface, are fixed in the layer structure. Furthermore, such layers are characterized by high loading densities of the immunological binding partner, rapid absorbency and low liquid requirements.

The particles should be smaller than the pores of the structure in which they are embedded. Preferred average diameters are from about 0.05 to about $5\mu$ and especially preferred are particles ranging from about 0.34 to about 1.04 in diameter.

In an especially advantageous embodiment of the present invention, a glass fiber-containing fleece is used as starting material for the fixing layer. The glass fiber content is preferably at least 60%. In this case, too, the immunological binding partner is preferably fixed on particles which, preferably according to the above-described impregnation process, are embedded in the glass fiber layer. Such a glass fiber fleece is characterized by good transport properties and can be produced in very thin layers. Advantageously, these layers are strengthened by the addition of polyvinyl alcohol in the manner described in U.S. Pat. No. 4,788,152. A further advantage of the glass fibers is the comparatively low non-specific binding of immune reagents on the glass fiber surface. Furthermore, as is described in U.S. Pat. No. 4,477,575, glass fibers can be used for separating off red blood coloured material (erythrocytes) from whole blood. Test carriers can be produced therewith which can prepare the blood eliminating the need to obtain a plasma or serum sample from the whole to be analyzed.

The present invention will now be described in more detail with reference to embodiments illustrated schematically in the Figures, in which:

FIG. 1 shows a first embodiment of a test carrier according to the present invention in section; and FIG. 2 shows a second embodiment of a test carrier according to the present invention in section.

In the case of the test carrier 1 illustrated in FIG. 1, a conjugate layer 2 and a fixing layer 3 are held by a frame 4. The frame 4 is preferably a synthetic resin injection molded part with a recess 5 in which runs an axle bar 6 of a synthetic resin joint. The axle bar 6 is part of a transparent synthetic resin carrier 7 to which is fixed an optical detection layer 8. The optical detection layer is covered with an optical barrier layer 9.

This FIG. 1 illustrates a first position of the optical detection layer 8 in which there is no contact with the fixing layer 3 so that no liquid can pass over. However, the synthetic resin carrier can be tilted about the axle bar 6 so that the optical barrier layer 9 comes into contact with the fixing layer 3. In this (not illustrated) second position, a liquid exchange can take place in a direction which is vertical to the contact surfaces between the optical detection layer 8 and the fixing layer 3 through the liquid-permeable optical barrier layer 9.

In the case of the test carrier 11 illustrated in FIG. 2, a fixing layer 13 is fixed on a base layer 20 which can consist, for example, of a stiff synthetic resin film such as is usual in the case of test strips. As a whole, the test carrier has a longitudinally extending shape similar to a test strip.

In the longitudinal direction of the test carrier, a sample application region 21 and a detection region 22 are differentiated, the fixing layer 13 thereby extending from the sample application region 21 into the detection region 22.

In the sample application region 21, over the fixing layer 13, a porous conjugate layer 12 and an erythrocyte separation layer 23 are disposed. Both are so fixed with a melt adhesive strip 24 that they lay full-facedly on one another so that liquid exchange between the layers 23, 12, 13 is possible.

In the detection region 22, the fixing layer 13 is bridged over by a flap 25 which consists of a transparent, flexible synthetic resin carrier film 17, an optical detection layer 17 and an optical barrier layer 19. The flap 25 is securely held by a melt adhesive strip 26 in such a manner that, in the illustrated first position, the optical detection layer 18 has no liquid exchange contact with the fixing layer 13. However, by means of external manipulation, for example manually or with the help of an apparatus, the flap 25 can be pressed downwardly. An appropriate device is described in U.S. Pat. No. 4,780,283. When the flap 25 is pressed against the fixing layer 13, liquid exchange can take place between the fixing layer 13 and the optical detection layer 18 (second position).

The function is similar in the case of both test carriers.

A sample which contains a component to be determined (analyte) is brought into contact with the conjugate layer 2, 12. In the case of FIG. 2, this takes place indirectly, the sample being applied to the erythrocyte separation layer 23. While it trickles through the layer 23, erythrocytes are separated off so that essentially only plasma (with the analyte) gets into the conjugate layer 12 (cf. U.S. Pat. No. 4,477,575).

In order, for example, to determine a free antigen or hapten Agf (f for "free") contained in a sample, the conjugate layer 12 contains an antibody Ab for this antigen or hapten which is conjugated with an appropriate labelling enzyme. The conjugate AbE is dissolved by the sample penetrating into the layer and the specific binding reaction thereby begins, i.e. Agf-AbE complexes are formed.

For the present invention, it is not necessary that the binding reaction between Agf and AbE proceeds far before both penetrate with the sample liquid into the fixing layer 3, 13. On the contrary, the fixing layer 3, 13 is so designed that the liquid spreads out quickly therein.

In the illustrated example, the fixing layer 13 contains a carrier-fixed antigen Agb (b for "bound") which corresponds to the antigen in the sample or is analogous with this, i.e. binds with the same antibody, so that carrier-fixed Agb-AbE complexes form.

Due to the rapid spreading out of the liquid in the fixing layer 3, 13, the fixing layer uniformly wetted and contains, at the beginning of the reaction, about the same concentration of the reaction components. Thus, the layer 3, 13 practically forms a kind of cuvette for the reaction mixture in which the binding reaction between the participating immunological binding partners takes place spatially homogeneously.

Only after completion of a desired incubation time, which is adjusted to the requirements of the particular test, is the optical detection layer 8, 18 brought into the second position and thus into liquid contact with the fixing layer 3, 13.

The sample liquid with the therein contained Agf-AbE complexes thereby gets into the optical detection layer. The enzyme there produces a color change of the substrate. The speed of the color change is characteristic of the concentration of the enzyme and thus for the concentration of the analyte. Due to the fact that the optical detection layer 8, 18 is brought with its whole surface into liquid contact with the fixing layer 3, 13, uniform transfer into the optical detection layer is obtained and thus homogeneous color formation which is measured photometrically through the transparent carrier 7, 17, i.e. on the side of the optical detection layer 8, 18 facing away from the fixing layer 3, 13 can be detected.

Since the usual color-forming substrates are soluble, the penetration of the sample liquid into the optical detection layer has the result that substrate can also pass backwards into the fixing layer. This produces a disturbing color formation in the fixing layer because of the carrier-fixed enzyme there present. In order to avoid disturbing influences on the optical measurement, an optical barrier layer is provided between the optical detection layer and the fixing layer. It consists for example, of a porous structure which contains a pigment, preferably titanium dioxide. Such a two-layered construction of optical barrier layer 9, 19 and optical detection layer 8, 18 is known in the test carrier art and therefore need not be explained here in detail.

Instead of the described two-layered construction, it is also possible to use an optical detection layer which itself contains a sufficiently high pigment concentration in order to prevent disturbance of the measurement by color formation in the fixing layer. This too, is a known mode of measurement in test carrier technology but, is less preferred in comparison with the two-layered construction. The two-layered construction of this invention with the use of a thin optical detection layer, leads to strong color formation even when small sample volumes are used.

As already mentioned, the suction force of the fixing layer 3, 13 should be greater than that of the conjugate layer 2, 12. Insofar as the test carrier has further layers upstream, such as in the case of FIG. 2 the erythrocyte separation layer 23, their suction force should also be smaller than that of the fixing layer. The layers placed upstream are thereby substantially sucked empty by the fixing layer and it is possible to work with an especially small sample volume.

The present invention can also be used for analysis processes other than those here described in detail herein. For example in some cases, the free antigen Agf is not itself the analyte. On the contrary, it is possible to carry out tests in which preceding reactions lead to the formation of a concentration of free antigen which, of its part, is characteristic for the concentration of the original analyte. Naturally, a test course is also possible in which antigens and antibodies are exchanged. Thus, e.g., for the detection of a free antibody, an antigen conjugate is used in the conjugate layer and a carrier-fixed antibody in the fixing layer. The quantity of the reagents in the test layers depends on the specific test. In particular, with respect to the necessary amount of the immunological reagents, their mutual affinity has to be taken into account. As with all procedures in this art, optimum quantities are determined experimentally.

The embodiment illustrated in FIG. 2 is preferred to the embodiment illustrated in FIG. 1 because it is an especially simple to produce. In the fixing layer, a longitudinal transport of the liquid parallel to the layer surface takes place in a layer which can be used at the same time for separating off erythrocytes. The construction makes it possible to use very thin layers so that, in all, analyses are possible with a very small sample volume of, for example, 30 $\mu$l. The fixing layer preferably has a thickness of from 50 to 500$\mu$ and especially preferably of less than 300$\mu$.

The following Examples are given for the purpose of illustrating the present invention:

EXAMPLE 1

Theophylline test

A test carrier with the principle construction according to FIG. 2 is produced as follows:

Production of the conjugate layer 12

Anti-theophylline AB, conjugated with β-galactosidase, is impregnated in phosphate buffered saline (PBS) with 1% Crotein C (Croda GmbH, Nettetal, Federal Republic of Germany (FRG)) on to stencil paper (Schoeller & Hoesch, Gernsbach, FRG) so that 1 U of enzyme activity is available per $cm^2$.

Production of the fixing layer 13

Latex particles are first loaded with an analyte analogue as follows: A 10% stabilized suspension of calibrated latex (diameter 0.66 μm., Rhone-Poulenc, Aubervilliers, France) is sucked through a G5 frit under vacuum. The latex particles remaining behind in front of the frit are resuspended in distilled water and mixed with 25 mg. N-ethylmorpholinocarbodiimide/g. of latex. After 30 minutes, 20 mg. polyhapten per gram of latex are incubated with the latex overnight. Initially, the pH is tested and adjusted to about 5. As polyhapten, a non-specific antibody to which theophylline is covalently coupled according to known processes is used. The linker molecule is chosen so that, according to Federal Republic of Germany Patent Specification No. 35 24 464, the affinity of the antibody used to the polyhapten is considerably higher than to the free theophylline. Loading of about 4 μg. polyhapten/g. of latex is achieved.

The so produced polyhapten-loaded latex particles are suspended 10% in PBS (+0.05% detergent "Brij 58", Serva, Heidelberg, FRG). A glass fiber fleece is impregnated with the suspension, the fleece being produced as follows:

As starting materials, there are used:
1000 l. distilled water
1.0 kg. glass fiber type 108 A (John Mansville, Denver, U.S.A.)
0.05 kg. polyvinyl alcohol type Kuralon VPB 105-2 (Rohtext Textil GmbH, Mönchengladbach, FRG).

A sloping sieve machine is used for the production of the fleece. The fiber materials are brushed out as 0.1% mixture, the fibre material being pumped on to a sloping sieve. While the liquid flows off or is sucked off by vacuum, the fibers orientate on the sieve surface and are dried as fleece over drying cylinders. Drying takes place at 125° C. until an end moisture of 0.5 to 1.5% by weight is achieved. The sucking off and transport speeds are so chosen that a material results with a weight per unit surface area of 30 g./$m^2$ and a thickness of 0.25 mm.

Production of erythrocyte separation fleece 23

The erythrocyte separation fleece is produced in the same way as the glass fibre fleece serving as a basis for the fixing layer.

Production of the optical detection layer 18 and of the optical barrier layer 19 in combination A coating mass is produced with the following composition:

| | |
|---|---|
| Propiofan 70 D (BASF Ludwigshafen, FRG) | 17 g. |
| Texamid 578 (Kelco, Hamburg, FRG) 83, 1% | 1.44 g. |
| kieselguhr | 11 g. |
| chlorophenol red galactoside (Boehringer Mannheim, FRG) | 0.88 g. |
| buffer (PBS with 5 mM magnesium chloride) | 68.5 g. |
| | 100 g. |

This coating mass is applied to a base layer of Pokalon (layer thickness 200 μm., Lonza) and coated out ("raked") to a wet film thickness of 150 μm.

The coating mass for the optical barrier film contains the following components:

| | |
|---|---|
| Propiofan 70 D (BASF Ludwigshafen, FRG) | 19.0 g. |
| Texamid 578 (83.1%) | 0.5 g. |
| kieselguhr | 36.1 g. |
| titanium dioxide RN 56 (Kronos AG, Leverkusen, FRG) | 7.5 g. |
| PBS (with 5 mM magnesium chloride) | 76.0 g. |
| Triton X 100 (Serva) | 0.3 g. |
| | 140.0 g. |

The coating mass is applied to an optical detection film, previously dried at 50° C. for 45 minutes, and with 250 μm. wet film thickness. The drying takes place under the same conditions as before.

The components of the test carrier have approximately the following dimensions:

| | |
|---|---|
| erythrocyte separation layer: | 6 × 6 mm. |
| conjugate layer: | 7 × 6 mm. |
| fixing layer: | 17 × 6 mm. |
| flap 25: | 15 × 6 mm. |

Detection of theophylline

30 μl. of sera with different theophylline concentrations are applied. The strips are placed in a "Reflotron" apparatus (Boehringer Mannheim GmbH, FRG). The time from the application of the sample up to the complete spreading out on the fixing layer is at most about 30 seconds. After about 180 seconds, the incubation time of the immunological binding partners is completed and the flap 25 is pressed against the fixing layer 13. After about 230 seconds, the remission is measured at a wavelength of $\lambda = 567$ nm. The following values are thereby obtained:

| c (Theo)/mg./l. | % R |
|---|---|
| 0 | 55.3 |
| 2 | 51.0 |
| 6 | 47.5 |
| 10 | 44.0 |
| 24 | 39.5 |
| 30 | 37 |
| 45 | 35 |

The achieved gradation in the clinically relevant measurement range of theophylline (2–30 mg./l.) is fully sufficient to make possible precise determination of the parameter.

EXAMPLE 2

T-Uptake test

Production of the conjugate layer

In this case, the conjugate layer contains T4 conjugated with β-galactosidase. Otherwise, the layer production is analogous to Example 1, an enzyme activity of 0.1 U/$cm^2$ thereby being adjusted.

Production of the fixing layer

The fixing layer is produced analogously to Example 1, except that titanium dioxide particles are used as carrier for the carrier-fixed second binding partner:

10 g. Titanium dioxide (RN 43, Kronos Titan, Leverkusen, FRG) are stirred for 2 hours in 400 ml. water, which is adjusted with acetic acid to pH 3.5, and with 4 ml. GFZO-silane (3-triethoxysilylpropyl)-succinic anhydride; Wacker-Chemie, München, FRG). Thereafter, the liquid is sucked through a frit under vacuum, followed by a multiple washing with water and drying for 1 hour at 140° C.

To the so produced COOH-modified titanium dioxide are coupled anti-TBG antibodies in a manner analogous to that used in Example 1, via carbodiimide (5 mg. AB/g. latex). The antibody-loaded titanium dioxide is impregnated 25% (w/v) into a glass fibre fleece produced analogously to Example 1.

The optical detection layer 18 and the optical barrier layer 19 are the same as in Example 1.

T4-Uptake analysis

30 μl. of samples (sera) with different TBG concentrations are applied; the strip is, as in the case of Example 1, placed in a "Reflotron" apparatus. In this case, the filling of the fixing layer is concluded after 30 seconds at the latest. The closure of the flap takes place after 150 seconds. The remission measurement takes place at $\lambda = 567$ nm after 230 seconds. The following measurement results are obtained:

| TBG sample | % R |
| --- | --- |
| buffer (=0 TBG) | 29.8 |
| "TBG-free serum" ($\leq 0.05$ μmol/l.) | 33.2 |
| normal serum (about 0.25 μmol/l.) | 42.2 |
| pathologically increased serum (about 0.42 μmol/l.) | 50.8 |

In this case, too, there is achieved a very good gradation of very low TBG values up to increased TBG values.

We claim:

1. Test carrier useful in determination of an analyte in a liquid sample, comprising:
   (i) a liquid absorbing first layer which contains a soluble conjugate of a first immunological binding partner and a label, the immunological binding partner of which specifically binds to said analyte to form a complex of analyte and conjugate;
   (ii) a porous second layer in permanent fluid communication with said first layer and containing a solid phase bound analyte or analyte analogue which binds to said first immunological binding partner but does not specifically bind with said analyte, wherein said second layer absorbs liquid at a rate which spreads liquid therethrough in an amount of time less than an amount of time necessary for completion of a binding reaction between said solid phase bound analyte or analyte analogue and any of first immunological binding partner not bound to analyte, and
   (iii) a third, liquid absorbing layer which contains a reagent which reacts with any conjugate of first immunological binding partner and label bound to said analyte to form an optically detectable signal, wherein said third layer is positioned on a flap means in said test carrier so that it is not in permanent contact with said second layer but may be brought into contact therewith as desired to permit liquid flow from said second layer to said third layer said contact permitting passage of liquid containing said complex of analyte and conjugate from said second layer into said third layer and penetration therein, to form said optically detectable signal.

2. Test carrier of claim 1, wherein said third layer is positioned in said carrier to permit contact from top or bottom of said second layer.

3. Test carrier of claim 1, wherein said second layer is characterized by a rate of liquid absorption greater than a rate of liquid absorption of said first layer.

4. Test carrier of claim 1, wherein a surface of said third layer faces said second layer, said surface being covered by a fourth layer which forms an optical barrier but is permeable to a liquid.

5. Test carrier of claim 1, wherein said second layer comprises a fiber composite structure.

6. Test carrier of claim 5, wherein said fiber composite structure is a fleece.

7. Test carrier of claim 5, wherein said fiber composite structure comprises synthetic resin fibers.

8. Test carrier of claim 5, wherein said fiber composite structure comprises glass fibers.

9. Test carrier of claim 8, wherein said fiber composite structure contains polyvinyl alcohol.

10. Test carrier of claim 1 or 5, wherein said second binding partner is bound to particles embedded in said second layer.

11. Test carrier of claim 1, wherein said particles consist of a synthetic resin.

12. Test carrier of claim 10, wherein said particles consist of inorganic material.

13. Test carrier of claim 10, wherein said particles have an average diameter of from about 0.01 u to about 5 u.

14. Test carrier of claim 13, wherein said particles have an average diameter of from about 0.3 u to about 1 u.

15. Test carrier of claim 1, further comprising a support layer to which said second layer is fixed, said second layer being defined by a sample application region at one end and an optical determination region at the other end, wherein said first layer is positioned in said sample application region and said third layer is positioned to permit contact with said second layer in said optical detection region.

16. Method for determination of an analyte in a liquid sample comprising contacting a liquid sample to a test carrier as in claim 1, incubating said sample to favor binding between (i) said analyte or a reaction product of said analyte and said conjugate and (ii) said conjugate and said second binding partner, and determining an optical change in said third layer as a measure of said analyte in said sample.

17. Process according to claim 16, wherein the liquid runs in the fixing layer parallel to its surface.

* * * * *

UNITED STATES PATENT AND TRADEMARK OFFICE
CERTIFICATE OF CORRECTION

PATENT NO. : 5,071,746
DATED : December 10, 1991
INVENTOR(S) : Hans-Erich Wilk et al.

It is certified that error appears in the above-identified patent and that said Letters Patent is hereby corrected as shown below:

```
Column 1, line 25:  after "form" add -- and is --;
          line 33:  after "layer" add -- takes place --;
          line 35:  delete "takes place".

Column 5, line 43:  change "4,258,001" to -- 4,613,567 --;
          lines 67-68:  change "0.34 to about "1.04" to
0.3µ to about 1.0µ --.
```

Signed and Sealed this

Twenty-second Day of June, 1993

Attest:

MICHAEL K. KIRK

Attesting Officer

Acting Commissioner of Patents and Trademarks